(12) United States Patent
Kreutzer et al.

(10) Patent No.: US 7,473,525 B2
(45) Date of Patent: Jan. 6, 2009

(54) COMPOSITIONS AND METHODS FOR INHIBITING EXPRESSION OF ANTI-APOPTOTIC GENES

(75) Inventors: Roland Kreutzer, Weidenberg (DE); Stefan Limmer, Neudrossenfeld (DE); Hans-Peter Vornlocher, Bayreuth (DE); Philipp Hadwiger, Bayreuth (DE); Anke Geick, Bayreuth (DE); Matthias Ocker, Erlangen (DE); Christoph Herold, Erlangen (DE); Detlef Schuppan, Bubenreuth (DE)

(73) Assignee: Alnylam Europe AG, Cambridge, MA (US)

( * ) Notice: Subject to any disclaimer, the term of this patent is extended or adjusted under 35 U.S.C. 154(b) by 768 days.

(21) Appl. No.: 10/384,260

(22) Filed: Mar. 7, 2003

(65) Prior Publication Data

US 2004/0001811 A1  Jan. 1, 2004

Related U.S. Application Data

(63) Continuation-in-part of application No. PCT/EP02/00151, filed on Jan. 9, 2002.

(30) Foreign Application Priority Data

Jan. 9, 2001  (DE)  ................. 101 00 586

(51) Int. Cl.
*C12Q 1/68* (2006.01)
*C12P 19/34* (2006.01)
*C12N 5/00* (2006.01)
*C12N 5/02* (2006.01)
*C07H 21/02* (2006.01)
*C07H 21/04* (2006.01)

(52) U.S. Cl. ............... 435/6; 435/91.1; 435/325; 435/375; 536/23.1; 536/24.3; 536/24.33; 536/24.5

(58) Field of Classification Search ............... 514/44; 435/6, 91.1, 325, 375; 536/23.1, 24.3, 24.5
See application file for complete search history.

(56) References Cited

U.S. PATENT DOCUMENTS 4,868,116 A  9/1989  Morgan et al.

(Continued)

FOREIGN PATENT DOCUMENTS

DE  199 03 713  1/1999

(Continued)

OTHER PUBLICATIONS

Cioca et al. RNA interference is a functional pathway with therapeutic potential in human myeloid leukemia cell lines. Cancer Gene Therapy, 2003 vol. 10:125-133.*

(Continued)

*Primary Examiner*—Sean McGarry
*Assistant Examiner*—Terra Cotta Gibbs
(74) *Attorney, Agent, or Firm*—Lowrie, Lando & Anastasi, LLP

(57) ABSTRACT

The present invention relates to a double-stranded ribonucleic acid (dsRNA) for inhibiting the expression of an anti-apoptotic gene, comprising a complementary RNA strand having a nucleotide sequence which is less that 25 nucleotides in length and which is substantially identical to at least a part of an apoptotic gene, such as a Bcl gene. The invention also relates to a pharmaceutical composition comprising the dsRNA together with a pharmaceutically acceptable carrier; methods for treating diseases caused by the expression of an anti-apoptotic gene using the pharmaceutical composition; and methods for inhibiting the expression of an anti-apoptotic gene in a cell.

4 Claims, 3 Drawing Sheets

U.S. PATENT DOCUMENTS

| | | | |
|---|---|---|---|
| 4,980,286 A | 12/1990 | Morgan et al. | |
| 4,987,071 A | 1/1991 | Cech et al. | |
| 5,107,065 A | 4/1992 | Shewmaker et al. | |
| 5,190,931 A | 3/1993 | Inouye | |
| 5,208,149 A | 5/1993 | Inouye | |
| 5,212,295 A | 5/1993 | Cook | |
| 5,254,678 A | 10/1993 | Haseloff et al. | |
| 5,328,470 A | 7/1994 | Nabel et al. | |
| 5,521,302 A | 5/1996 | Cook | |
| 5,587,361 A | 12/1996 | Cook et al. | |
| 5,674,683 A | 10/1997 | Kool | |
| 5,712,257 A | 1/1998 | Carter | |
| 5,719,271 A | 2/1998 | Cook et al. | |
| 5,998,203 A | 12/1999 | Matulic-Adamic et al. | |
| 6,025,167 A | 2/2000 | Cech et al. | |
| 6,054,299 A | 4/2000 | Conrad | |
| 6,127,533 A | 10/2000 | Cook et al. | |
| 6,166,197 A | 12/2000 | Cook et al. | |
| 6,271,358 B1 | 8/2001 | Manoharan et al. | |
| 6,423,489 B1 | 7/2002 | Anderson et al. | |
| 6,486,299 B1 | 11/2002 | Skimkets | |
| 6,506,559 B1 | 1/2003 | Fire et al. | |
| 2002/0086356 A1 | 7/2002 | Tuschl et al. | |
| 2002/0114784 A1 | 8/2002 | Li et al. | |
| 2002/0123034 A1 | 9/2002 | Canaani et al. | |
| 2002/0132346 A1 | 9/2002 | Cibelli | |
| 2002/0162126 A1 | 10/2002 | Beach et al. | |
| 2002/0173478 A1 | 11/2002 | Gewirtz | |
| 2003/0027783 A1 | 2/2003 | Zernicka-Goetz et al. | |
| 2003/0108923 A1 | 6/2003 | Tuschl et al. | |
| 2003/0125281 A1 | 7/2003 | Lewis et al. | |
| 2003/0143732 A1 | 7/2003 | Fosnaugh et al. | |
| 2003/0148341 A1 | 8/2003 | Sin et al. | |
| 2003/0157030 A1 | 8/2003 | Davis et al. | |
| 2003/0176671 A1 | 9/2003 | Reed et al. | |
| 2003/0180756 A1 | 9/2003 | Shi et al. | |
| 2003/0190635 A1 | 10/2003 | McSwiggen | |
| 2003/0198627 A1 | 10/2003 | Arts et al. | |
| 2004/0072779 A1* | 4/2004 | Kreutzer et al. | 514/44 |
| 2006/0258608 A1 | 11/2006 | Meyers | |

FOREIGN PATENT DOCUMENTS

| | | |
|---|---|---|
| DE | 199 56 568.6 | 11/1999 |
| DE | 102 35 620.3 | 8/2002 |
| EP | 1 144 623 B1 | 8/2002 |
| EP | 1 230 375 B1 | 7/2005 |
| WO | WO 89/02468 | 3/1989 |
| WO | WO 89/05345 | 6/1989 |
| WO | WO 89/07136 | 8/1989 |
| WO | WO 92/07573 | 5/1992 |
| WO | WO 92/19732 | 11/1992 |
| WO | WO 94/01550 A3 | 1/1994 |
| WO | WO 98/05770 | 2/1998 |
| WO | WO 98/53083 | 11/1998 |
| WO | WO 99/15682 | 4/1999 |
| WO | WO 99/32619 | 7/1999 |
| WO | WO 99/49029 | 9/1999 |
| WO | WO 99/53050 | 10/1999 |
| WO | WO 99/61631 | 12/1999 |
| WO | WO 00/01846 | 1/2000 |
| WO | WO 00/22113 | 4/2000 |
| WO | WO 00/22114 | 4/2000 |
| WO | WO 00/44495 | 8/2000 |
| WO | WO 00/44895 | 8/2000 |
| WO | WO 00/44914 | 8/2000 |
| WO | WO 00/63364 | 10/2000 |
| WO | WO 00/68374 | 11/2000 |
| WO | WO 01/18197 A1 | 3/2001 |
| WO | WO 01/29058 A1 | 4/2001 |
| WO | WO 01/36646 A1 | 5/2001 |
| WO | WO 01/42443 A1 | 6/2001 |
| WO | WO 01/48183 A2 | 7/2001 |
| WO | WO 01/68836 A2 | 9/2001 |
| WO | WO 01/70949 A1 | 9/2001 |
| WO | WO 01/75164 A2 | 10/2001 |
| WO | WO 01/92513 A1 | 12/2001 |
| WO | WO 02/16620 A2 | 2/2002 |
| WO | WO 02/26780 A2 | 4/2002 |
| WO | WO 02/44321 A2 | 6/2002 |
| WO | WO 02/055692 A2 | 7/2002 |
| WO | WO 02/055693 A2 | 7/2002 |
| WO | WO 02/061034 A2 | 8/2002 |
| WO | WO 02/068635 A2 | 9/2002 |
| WO | WO 02/068637 A2 | 9/2002 |
| WO | WO 03/006477 A1 | 1/2003 |
| WO | WO 03/012052 A2 | 2/2003 |
| WO | WO 03/012082 A2 | 2/2003 |
| WO | WO 03/016572 A1 | 2/2003 |
| WO | WO 03/033700 | 4/2003 |
| WO | WO 03/035082 | 5/2003 |
| WO | WO 03/035083 | 5/2003 |
| WO | WO 03/035868 | 5/2003 |
| WO | WO 03/035869 | 5/2003 |
| WO | WO 03/035870 | 5/2003 |
| WO | WO 03/035876 | 5/2003 |
| WO | WO 03/070283 A2 | 8/2003 |
| WO | WO 03/070750 A2 | 8/2003 |
| WO | WO 03/070969 A2 | 8/2003 |
| WO | WO 03/070972 A2 | 8/2003 |
| WO | WO 03/074654 A2 | 9/2003 |
| WO | WO 03/080794 A2 | 10/2003 |
| WO | WO 03/080807 A2 | 10/2003 |
| WO | 2004/015107 | 2/2004 |
| WO | 2004/027030 | 4/2004 |
| WO | 2004/045543 | 6/2004 |
| WO | WO 2004/065601 | 8/2004 |
| WO | WO 2005/012357 | 2/2005 |
| WO | WO 0044895 A1 | 8/2008 |

OTHER PUBLICATIONS

Williams et al. Thermodynamic comparison of the salt dependent of natural RNA hairpins and RNA hairpins with non-nucleotide spacers. Biochemistry, 1996 vol. 35:14665-14670.*

Aoki et al. RNA interference may be more potent than antisense RNA in human cancer cell lines. Clinical and Experimental Pharmacology and Physiology, 2003 vol. 30:96-102.*

International Search Report PCT/EP 02/00151.

Caplen, N.J., (2002), "A new approach to the inhibition of gene expression", *Trends in Biotechnology*, 20(2):49-51.

Caplen, N.J. et al., (2001), "Specific inhibition of gene expression by small double-stranded RNAs in invertebrate and vertebrate systems", *Proc. Natl. Acad. Sci. USA*, 98(17):9742-9747.

Doench, J.G. et al., (2003), "siRNAs can function as miRNAs", *Genes & Development*, 17:438-442.

Donzé, O. et al., (2002), "RNA interference in mammalian cells using siRNAs synthesized with T7 RNA Polymerase", *Nucleic Acids Research*, 30(10):e46(4pages).

Elbashir, S.M. et al., (2001), "RNA interference is mediated by 21- and 22-nucleotide RNAs", *Genes & Development*, 15:188-200.

Elbashir, S.M. et al., (2001), "Functinal anatomy of siRNAs for mediating efficient RNAi in *Drosophila melanogaster* embryo lysate", *The EMBO Journal*, 20(23):6877-6888.

Fire, A. et al., (1998), "Potent and specific genetic interference by double-stranded RNA in *Caenorhabditis elegans*", *Nature*, 391:806-811.

Harborth, J. et al., (2001), "Identification of essential genes in cultured mammalian cells using small interfering RNAs", *Journal of Cell Science*, 114(24):4557-4565.

Lewis, D.L. et al., (2002), "Efficient delivery of siRNA for inhibition of gene expression in postnatal mice", *Nature Genetics*, 32:107-108.

Manche, L. et al., (1992), "Interactions between Double-Stranded RNA Regulators and the Protein Kinase DAI", *Molecular and Cellular Biology*, 12(11):5238-5248.

McCaffrey, A.P. et al., (2002), "RNA interference in adult mice", *Nature*, 418:38-39.

Ngô, H. et al., (1998), "Double-stranded RNA induces mRNA degradation in *Trypanosoma brucei*", *Proc. Natl. Acad. Sci.*, 95:14687-14692.

Paddison, P.J. et al., (2002), "Short hairpin RNAs (shRNAs) induce sequence-specific silencing in mammalian cells", *Genes & Development*, 16:948-958.

Randall, G. et al., (2003), "Clearance of replicating hepatitis C virus replicon RNAs in cell culture by small interfering RNAs", *PNAS*, 100(1):235-240.

Tijsterman, M. et al., (2002), "The Genetics of RNA Silencing", *Annu. Rev. Genet.*, 36:489-519.

Yu, J. et al., (2002), "RNA interference by expression of short-interfering RNAs and hairpin RNAs in mammalian cells", *PNAS*, 99(9):6047-6052.

Holen, T. et al., (2002), "Positional effects of short interfering RNAs targeting the human coagulation trigger Tissue Factor", *Nucleic Acids Research*, 30(8):1757-1766.

Ambros. V., (2001), "Dicing Up RNAs", *Science*, 293:811-813.

Elbashir, S.M. et al., (2001), "Duplexes of 21-nucleotide RNAs mediate RNA interference in cultured mammalian cells", *Nature*, 411:494-498.

Gautschi, O. et al., (2001), "Activity of a Novel bcl-2/bcl-xL-Bispecific Antisense Oligonucleotide Against Tumors of Diverse Histologic Origins", *Journal of the National Cancer Institute*, 93(6):463-471.

Lipardi, C. et al., (2001), "RNAi as Random Degradative PCR: siRNA Primers Convert mRNA into dsRNAs that Are Degraded to Generate New siRNAs", *Cell*, 107:297-307.

Sharp, P.A., (2001), "RNA interference—2001", *Genes & Development*, 15:485-490.

Sijen, T. et al., (2001), "On the Role of RNA Amplification in dsRNA-Triggered Gene Silencing", *Cell*, 107:465-476.

Bass, B.L., (2000), "Double-Stranded RNA as a Template for Gene Silencing", *Cell*, 101:235-238.

Cobaleda, C. et al., (2000), "In vivo inhibition by a site-specific catalytic RNA subunit of Rnase P designed against the BCR-ABL oncogenic products: a novel approach for cancer treatment", *Blood*, 95(3):731-737.

Hammond, S.M. et al., (2000), "An RNA-directed nuclease mediates post-transcriptional gene silencing in *Drosophia* cells", *Nature*, 404:293-296.

Yang, D. et al., (2000), "Evidence that processed small dsRNAs may mediate sequence-specific mRNA degradation during RNAi in *Drosophila* embryos", *Current Biology*, 10:1191-1200.

Wianny, F. et al., (2000), "Specific interference with gene function by double-stranded RNA in early mouse development", *Nature Cell Biology*, 2:70-75.

Zamore, P.D. et al., (2000), "RNAi: Double-Stranded RNA Directs the ATP-Dependent Cleavage of mRNA at 21 to 23 Nucleotide Intervals", *Cell*, 101:25-33.

Fire, A., (1999), "RNA-triggered gene silencing", *TIG*, 15(9):358-363.

Tuschl, T. et al., (1999), "Targeted mRNA degradation by double-stranded RNA in vitro", *Genes & Development*, 13:3191-3197.

Wild, K. et al., (1991), "The 2 Å structure of helix 6 of the human signal recognition particle RNA", *Structure*, (11):1345-1352.

Montgomery, M.K. et al., (1998), "Double-stranded RNA as a mediator in sequence-specific genetic silencing and co-suppression", *TIG*, 14(7):255-258.

Lowy, D.R. et al., (1993), "Function and Regulation of RAS", *Annu. Rev. Biochem.*, 62:851-891.

Downward, J. et al., (1990), "Identification of a nucleotide exchange-promoting activity for p21$^{ras}$", *Proc. Natl. Acad. Sci. USA*, 87:5998-6002.

Gibbs, J.B. et al., (1988), "Purification of ras GTPase activating protein from bovine brain", *Proc. Natl. Acad. Sci. USA*, 85:5026-5030.

International Search Report of International Application No. PCT/EP02/00151.

U.S. Appl. No. 60,117,635, Li et al. (filed Jan. 28, 1999).

U.S. Appl. No. 60/130,377, Pachuk et al. (filed Apr. 21, 1999).

Agrawal et al., "Self-Stabilized Oligonucleotides as Novel Antisense Agents" *Delivery Strategies for Antisense Oligonucleotide Therapeutics*, Edited by Saghir Akhtar, CRC Press, pp. 105-121 (1995).

Armentano et al., "Expression of human factor IX in rabbit hepatocytes by retrovirus-mediated gene transfer: Potential for gene therapy of hemophilia B" *Proc. Natl. Acad. Sci. USA* 87:6141-6145 (1990).

Bahramian et al., "Transcriptional and Posttranscriptional Silencing of Rodent α1(I) Collagen by a Homologous Transcriptionally Self-Silenced Transgene" *Mol. Cell. Biol* 19:274-283 (1999).

Barawkar et al., "Synthesis, biophysical properties, and nuclease resistance properties of mixed backbone oligodeoxynucleotides containing cationic internucleoside guanidinium linkages: Deoxynucleic guanidine/DNA chimeras" *Proc. Natl. Acad. Sci. USA* 95:11047-11052 (1998).

Barber et al., "Mutants of the RNA-Dependent Protein Kinase (PKR) Lacking Double-Stranded RNA Binding Domain I Can Act as Transdominant Inhibitors and Induces Malignant Transformation" *Mol. Cell. Biol*. 15:3138-3146 (1995).

Basbaum et al., "Focalized proteolysis: spatial and temporal regulation of extra cellular matrix degradation at the cell surface" *Curr. Opin. Cell Biol.* 8:731-738 (1996).

Beck, "Unknotting the Complexities of Multidrug Resistance: The Involvement of DNA Topoisomerases in Drug Action and Resistance" *J. Natl. Cancer Inst.* 81:1683-1685 (1989).

Berkner et al., "Development of Adenovirus Vectors for the Expression of Heterologous Genes" *BioTechniques* 6(7):616-629 (1998).

Bhan et al,. "2',5'-Linked oligo-3'-deoxyribonucleoside phosphorothioate chimeras: thermal stability and antisense inhibition of gene expression" *Nucleic Acids Res.* 25:3310-3317 (1997).

Billy et al., "Specific interference with gene expression induced by long, double-stranded RNA in mouse embryonal teratocarcinoma cell lines" *Proc. Natl. Acad. Sci. USA* 98:14428-14433 (2001).

Birkedal-Hansen et al., "Matrix Metalloproteinases: A Review" *Crit. Rev.Oral Biol. Med.* 4:197-250 (1993).

Borecky et al., "Therapeutic use of double-stranded RNAs in man" *Tex. Rep. Biol. Med.* 41:575-581 (1981-1982) (Abstract only).

Boyd, "Invasion and metastasis" *Cancer Metastasis Rev.* 15:77-89 (1996).

Braasch et al., "Locked nucleic acid (LNA): fine-tuning the recognition of DNA and RNA" *Chem. Biol.* 8:1-7 (2001).

Braich et al., "Regiospecific Solid-Phase Synthesis of Branched Oligonucleotides. Effect of Vicinal 2',5'- (or 2',3'-) and 3',5'-Phosphodiester Linkages on the Formation of Hairpin DNA" *Bioconjug. Chem.* 8:370-377 (1997).

Brennicke et al., "RNA editing" *FEMS Microbiology Reviews* 23:297-316 (1999).

Brinckerhoff et al., "Matrix metalloproteinases: a tail of a frog that became a prince" *Nature Reviews* 3:207-214 (2002).

Bucchini et al., "Pancreatic Expression of Human Insulin Gene in Transgenic Mice" *PNAS USA* 83:2511-2515 (1986).

Byrom et al., "Inducing RNAi with siRNA Cocktails Generated by RNase III" *TechNotes 10* (1), Ambion website (2004).

Chao et al., "BCL-2 Family: Regulators of Cell Death" *Annu. Rev. Immunol.* 16:395-419 (1998).

Chen et al., "Gene therapy for brain tumors: regression of experimental gliomas by adenovirus-mediated gene transfer in vivo" *Proc. Natl. Acad. Sci. USA* 91:3054-3057 (1994).

Chien et al., "Novel cationic cardiolipin analogue-based liposome for efficient DNA and small interfering RNA delivery in vitro and in vivo" *Cancer Gene Therapy* pp. 1-8 (2004).

Childs et al., "The MDR Superfamily of Genes and Its Biological Implications" *Imp. Adv. Oncol.* 21-36 (1994).

Chowdhury et al., "Long-Term Improvement of Hypercholesterolemia After Ex Vivo Gene Therapy in LDLR-Deficient Rabbits" *Science* 254:1802-1805 (1991).

Cole et al., "Overexpression of a Transporter Gene in Multidrug-Resistant Human Lung Cancer Cell Line" *Science* 258:1650-1654 (1992).

Cone et al., "High-efficiency gene transfer into mammalian cells: Generation of helper-free recombinant retrovirus with broad mammalian host range" *Proc. Natl. Acad. Sci. USA* 81:6349-6353 (1984).

Cook, "Medicinal chemistry of antisense oligonucleotides—future opportunities" *Anti-Cancer Drug Design* 6:585-607 (1991).

Cornetta et al., "Safety Issues Related to Retroviral-Mediated Gene Transfer in Humans" *Human Gene Therapy* 2 (1):5-14 (1991).

Couture et al., "Anti-gene therapy: the use of ribozymes to inhibit gene function" *Trends in Genetics* 12:510-515 (1996).

Couzin, "Small RNAs Make Big Splash" *Science* 298:2296-2297 (2002).

Crooke et al., "Pharmacokinetic Properties of Several Novel Oligonucleotide Analogs in Mice" *J. Pharmacol. Exp. Ther.* 277:923-937 (1996).

Czauderna et al., "Structural variations and stabilizing modifications of synthetic siRNAs in mammalian cells" *Nucleic Acids Res.* 31:1-12 (2003).

Dai et al., "Gene therapy via primary myoblasts: Long-term expression of factor IX protein following transplantation in vivo" *Proc. Natl. Acad. Sci. USA* 89:10892-10895 (1992).

Danos et al., "Safe and efficient generation of recombinant retroviruses with amphotropic and ecotropic host ranges" *Proc. Natl. Acad. Sci. USA* 85:6460-6464 (1988).

D'Ari, "Cycle-regulated genes and cell cycle regulation" *Bioassays* 23:563-565 (2001).

Delgado et al., "The Uses and Properties of PEG-Linked Proteins" *Crit. Rev. Therap. Drug Carrier Sys.* 9:249-304 (1992).

Dellweg et al., ed., *Römpp Lexikon Biotechnologie*, p. 354 and p. 673 (1992) (in German).

Docherty et al., "Nutrient regulation of insulin gene expression" *FASEB J.* 8:20-27 (1994).

Eder et al., "Monitoring of BCR-ABL expression using real-time RT-PCR in CML after bone marrow or peripheral blood stem cell transplantation" *Leukemia* 13:1383-1389 (1999).

Eglitis et al., "Gene Expression in Mice After High Efficiency Retroviral-Mediated Gene Transfer" *Science* 230:1395-1398 (1985).

Elbashir et al., "Analysis of gene function in somatic mammalian cells using small interfering RNAs" *Methods* 26:199-123 (2002).

Eriksson et al., "Establishment and characterization of mouse stain (TLL) that spontaneously develops T-cell lymphomas/leukemia" *Exp. Hematol.* 27:682-688 (1999).

Fallert-Müller, ed., *Encyclopedia of Biochemistry*, vol. J-Z, pp. 448-449 (2000) (in German).

Fan et al., "Reversal of Multidrug Resistance in Cancer", ed. Kellen, CRC, Boca Raton, FL, pp. 93-125.

Ferry et al., "Retroviral-mediated gene transfer into hepatocytes in vivo" *Proc. Natl. Acad. Sci. USA* 88:8377-8381 (1991).

Fotedar et al., "Apoptosis and the cell cycle" *Prog. Cell Cycle Res.* 2:147-163 (1996).

Gassmann et al., "Maintenance of an extrachomosomal plasmid vector in mouse embryonic stem cells" *PNAS USA* 92:1292-1296 (1995).

GenBank Accession No. M13994, "Human B-cell leukemia/lymphoma 2 (bcl-2) proto-oncogene mRNA encoding bcl-2-beta protein" Oct. 31, 1994.

GenBank Accession No. M13995, "Human B-cell leukemia/lymphoma 2 (bcl-2) proto-oncogene mRNA encoding bcl-2-beta protein" Oct. 31, 1994.

GenBank Accession No. U55763, "Cloning vector pEGFP-C1, complete sequence, enhanced green fluorescent protein (egfp) and neomycin phosphotransferase genes" Jun. 15, 1996.

Grasby et al., "Purine Functional Groups in Essential Residues of the Hairpin Ribozyme Required for Catalytic Cleavage of RNA" *Biochemistry* 34:4068-4076 (1995).

Griffey et al., "2'-O-Aminopropyl Ribonucleotides: A Zwitterionic Modification That Enhances the Exonuclease Resistance and Biological Activity of Antisense Oligonucleotides" *J. Med. Chem.* 39:5100-5109 (1996).

Gryaznov et al., "Template controlled coupling and recombination of oligonucleotide blocks containing thiophosphoryl groups" *Nucleic Acids Res.* 21:1403-1408 (1993).

Ha et al., "A bulged *lin-4/lin-14* RNA duplex is sufficient for *Caenorhabditis elegans lin-14* temporal gradient formation" *Genes & Development* 10:3041-3050 (1996).

Hamilton et al., "A Species of Small Antisense RNA in Postranscriptional Gene Silencing in Plants" *Science* 286:950-952 (1999).

Hamm et al., "Incorporation of 2'-Deoxy-2'mercaptocytidine into Oligonucleotides via Phosphoramidite Chemistry" *J. Org. Chem.* 62:3415-3420 (1997).

Hanahan et al., "The Hallmarks of Cancer" *Cell* 100:57-70 (2000).

Harris et al., "The Eµ-*myc* Transgenic Mouse A Model for High-incidence Spontaneous Lymphoma and Leukemia of Early B Cells" *J. Exp. Med.* 167(2):353-371 (1988).

Hedges, "The Origin and Evolution of Model Organisms" *Nature Reviews* 3:838-849 (2002).

Hoke et al., "Effects of phosphorothioate capping on antisense oligonucleotide stability, hybridization and antiviral efficacy versus herpes simplex virus infection" *Nucleic Acids Res.* 19:5743-5748 (1991).

Horn et al., "Chemical synthesis and characterization of branched oligodeoxyribonucleotides (bDNA) for use as signal amplifiers in nucleic acid quantification assays" *Nucleic Acids Res.* 25:4842-4849 (1997).

Hornung et al., "Sequence-specific potent induction of IFN-α by short interfering RNA in plasmacytoid dendritic cells through TLR7" *Nature Medicine* 11:263-270 (2005).

Hsu et al., "Immunogenicity of Recombinant Adenovirus-Respiratory Syncytial Virus Vaccines with Adenovirus Types 4, 5, and 7 Vectors in Dogs and a Chimpanzee" *J. Infectious Disease* 166:769-775 (1992).

Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma" *Cancer Res.* 65:8984-8992 (2005).

Huber et al., "Retroviral-mediated gene therapy for the treatment of hepatocellular carcinoma: An innovative approach for cancer therapy" *Proc. Natl. Acad. Sci. USA* 88:8039-8043 (1991).

Hunter et al., "The characteristics of inhibition of protein synthesis by double stranded ribonucleic acid in reticulocyte lysates" *J. Biol. Chem.* 250:409-417 (1975).

Hwu et al., "Functional and Molecular Characterization of Tumor-Infiltrating Lymphocytes Transduced with Tumor Necrosis Factor-α cDNA for the Gene Therapy of Cancer in Humans" *J. Immunol.* 150:4104-4115 (1993).

"InBase, The Intein Database: The Intein Registry—Inteins Sorted by Species" http://tools.neb.com/inbase/list.php (database updated on May 22, 2006).

International Preliminary Examination Report from PCT/DE00/00244.

"Introduction of DNA into Mammalian Cells" *Current Protocols in Molecular Biology*, Supplement 48, Edited Frederick M. Ausubel et al., John Wiley & Sons, Inc., pp. 9.4.7-9.4.8 (1999).

Iwas et al., "Gene regulation by decoy approach (1): synthesis and properties of photo-crosslinked oligonucleotides" *Nucleic Acids Symp. Ser.* 37:203-204 (1997).

James et al., "The Therapeutic Potential of Ribozymes" *Blood* 91:371-382 (1998).

Judge et al., "Sequence-dependent stimulation of the mammalian innate immune response by synthetic siRNA" *Natl. Biotechnol.* pp. 1-6 (2005) (8 pages of supplementary content included).

Kabanov et al., "A new class of antivirals: antisense oligonucleotides combined with a hydrophobic substituent effectively inhibit influenza virus reproduction and synthesis of virus-specific proteins in MDCK cells" *FEBS Lett.* 259(2):327-330 (1990).

Kay et al., "Hepatic Gene Therapy: Persistent Expression of Human α1-Antitrypsin in Mice after Direct Gene Delivery In Vivo" *Human Gene Therapy* 3:641-647 (1992).

Kennerdell et al., "Use of dsRNA-Mediated Genetic Interference to Demonstrate that *frizzled* and *frizzled 2* Act in the Wingless Pathway" *Cell* 95:1017-1026 (1998).

Kitabwalla et al., "RNA-Interference—A New Weapon Against HIV and Beyond" *N. Engl. J. Med.* 347:1364-1367 (2002).

Koshkin et al., "LNA (Locked Nucleic Acids)" Synthesis of the Adenine, Cytosine, Guanine, 5-Methylcytosine, Thymine and Uracil Bicyclonucleoside Monomers, Oligomerisation, and Unprecedented Nucleic Acid Recognition *Tetrahedron* 54:3607-3630 (1998).

Kovalchuk et al., "Burkitt Lymphoma in the Mouse" *J. Exp. Med.* 192:1183-1190 (2000).

Krepela, "Cysteine proteinases in tumor cell growth and apoptosis" *Neoplasma* 48:332-349 (2001).

Kreutzer et al., "Specific inhibition of viral gene expression by double-stranded RNA in vitro" *Annual Fall Meeting of the GBH*, Abstract for Poster Paper No. 328, p. S169 (1999).

Kumar et al., "Antisense RNA: function and fate of duplex RNA in cells of higher eukaryotes" *Microbiol. Mol. Biol. Rev.* 62:1415-1434 (1998).

Lee et al., "The *C. elegans* Heterochronic Gene *lin-4* Encodes Small RNAs with Antisense Complementarity to *lin-14*" *Cell* 75:843-854 (1993).

Letsinger et al., "Cholesteryl-conjugated oligonucleotides: Synthesis, properties, and activity as inhibitors of replication of human immunodeficiency virus in cell culture" *PNAS USA* 86:6553-6556 (1989).

Letter to the International Examining Authority from Gassner & Partner in the prosecution of PCT/DE00/00244 (WO 00/44895), 5 pages (Mar. 28, 2001) (in German).

Li et al., "Double-stranded RNA injection produces null phenotypes in zebrafish" *Dev. Biol.* 210:238, Abstract No. 346 (1999).

Lin et al., "Policing rogue genes" *Nature* 402:128-129 (1999).

Lipinski et al., "Experimental and computational approaches to estimate solubility and permeability in drug discovery and development settings" *Adv. Drug Deliv. Rev.* 23:3-25 (1997).

Ma et al., "Design and Synthesis of RNA Miniduplexes via a Synthetic Linker Approach" *Biochemistry* 32:1751-1758 (1993).

Majumdar et al., "Targeted gene knockout mediated by triple helix forming oligonucleotides" *Nat. Genet.* 20:212-214 (1998).

Manoharan, "Oligonucleotide Conjugates as Potential Antisense Drugs with Improved Uptake, Biodistribution, Targeted Delivery and Mechanism of Action" *Antisense and Nucleic Acid Drug Development* 12:103-128 (2002).

Manoharan et al., "Chemical Modifications to Improve Uptake and Bioavailability of Antisense Oligonucleotides" *Ann. NY Acad. Sci.* 660:306-309 (1992).

Manoharan et al., "Introduction of a Lipophilic Thioether Tether in the Minor Groove of Nucleic Acids for Antisense Applications" *Bioorg. Med. Chem. Lett.* 3(12):2765-2770 (1993).

Manoharan et al., "Cholic Acid-Oligonucleotide Conjugates for Antisense Applications" *Bioorg. Med. Chem. Lett.* 4(8):1053-1060 (1994).

Manoharan et al., "Oligonucleotide Conjugates Alteration of the Pharmacokinetic Properties of Antisense Agents" *Nucleosides & Nucleotides* 14:969-973 (1995).

Manoharan et al., "Lipidic Nucleic Acids" *Tetrahedron* 36:3651-3654 (1995).

Marques et al., "Activation of the mammalian immune system by siRNAs" *Nat. Biotechnol.*, 23(11):1399-1405 (2005).

Martinez et al., "Single-Stranded Antisense siRNAs Guide Target RNA Cleavage in RNAi" *Cell*, 110:563-574 (2002).

Maru, "Molecular Biology of Chronic Myeloid Leukemia" *Int. J. Hematol.* 73:308-322 (2001).

Matrisian, "Cancer biology: Extracellular proteinases in malignancy" *Curr. Biol.* 9 (20):R776-778 (1999).

McManus et al., "Gene Silencing in Mammals by Small Interfering RNAs" *Nat. Rev. Genet.*, 3:737-747 (2002).

Mendelsohn et al., "The EGF receptor family as target for cancer therapy" *Oncogene* 19(56):6550-6565 (2000).

Mignatti et al., "Biology and Biochemistry of proteinases in Tumor Invasion" *Physiol. Rev.* 73:161-195 (1993).

Milhaud et al., "Free and Liposome-Encapsulated Double-Stranded RNAs as Inducers of Interferon, Interleukin-6, and Cellular Toxicity" *J. Interferon Res.*, 11:261-265 (1991).

Minks et al., "Structural Requirements of Double-stranded RNA for the Activation of 2',5'-Oligo(A) Polymerase and Protein Kinase of Interferon-treated HeLa Cells" *J. Biol. Chem.* 254(20):10180-10183 (1979).

Mishra et al., "Improved leishmanicidal effect of phosphorotioate antisense oligonucleotides by LDL-mediated delivery" *Biochim. Biophys. Acta.* 1264:229-237 (1995).

Montgomery et al., "RNA as a target of double-stranded RNA-mediated genetic interference in *Caenorhabditis elegans*" *Proc. Natl. Acad. Sci. USA* 95:15502-15507 (1998).

Moss et al., "The Cold Shock Domain Protein LIN-28 Controls Developmental Timing in *C. elegans* and Is Regulated by the *lin-4* RNA" *Cell* 88:637-646 (1997).

Muellauer et al., "Mutations in apoptosis genes: a pathogenetic factor for human disease" *Mutat. Res.* 488:211-231 (2001).

Muzyczka, "Use of Adeno-Associated Virus as a General Transduction Vector for Mammalian Cells" *Curr. Topics Micro. Immunol.* 158:97-127 (1992).

Nielsen et al., "A novel class of conformationally restricted oligonucleotide analogues: synthesis of 2',3'-bridged monomers and RNA-selective hybridization" *Chem. Commun.* pp. 825-826 (1997).

Nikiforov et al., "Oligodeoxynucleotides containing 4-thiothymidine and 6-thiodeoxyguanosine as affinity labels for the Eco RV restriction endonuclease and modification methylase" *Nucleic Acids Res.* 20:1209-1214 (1992).

Normanno et al., "The role of EGF-Related Peptides in Tumor Growth" *Front. Biosci.* 6:D685-707 (2001).

Oberhauser et al., "Effective incorporation of 2'-O-methyl-oligoribonucleotides into liposomes and enhanced cell association through modification with thiocholestrol" *Nucl. Acids Res.* 20:533-538 (1992).

Obika et al., "Stability and structural features of the duplexes containing nucleoside analogues with a fixed N-type conformation, 2'-O,4'-C-methyleneribonucleosides" *Tetrahedron* 39:5401-5404 (1998).

Ouchi et al., "Synthesis and Antitumor Activity of Poly(Ethylene Glycol)s Linked to 5-Fluorouracil via a Urethane or Urea Bond" *Drug Design and Discovery* 9:93-105 (1992).

Pandolfi, "In vivo analysis of the molecular genetics of acute promyelocytic leukemia" *Oncogene* 20:5726-5735 (2001).

PCT/GB00/04404 as filed (Nov. 19, 1999).

Pegram et al., "Phase II Study of Receptor-Enhanced Chemosensitivity Using Recombinant Humanized Anti-p185[HER2]/neu Monoclonal Antibody Plus Cisplatin in Patients With HER2/neu-Overexpressing Metastatic Breast Cancer Refractory to Chemotherapy Treatment" *J. Clin. Oncol.* 16:2659-2671 (1998).

Perler, "InBase: the Intein Database" *Nucleic Acids Res.* 30:383-384 (2002).

Phillips et al., "The NZB Mouse as a Model for Chronic Lymphocytic Leukemia" *Cancer Res.* 52:437-443 (2000).

Pollock et al., "Mouse models of acute promyelocytic leukemia" *Curr. Opin. Hematol.* 8:206-211 (2001).

Polushin et al., "Synthesis of Oligonucleotides Containing 2'-Azido- and 2'-Amino-2'-deoxyuridine Using Phosphotriester Chemistry" *Tetrahedron* 37:3227-3230 (1996).

Ravasio, "Selective Hydrogenations Promoted by Copper Catalysts. 1. Chemoselectivity, Regioselectivity, and Stereoselectivity in the Hydrogenation of 3-Substituted Steroids" *J. Org. Chem.* 56:4329-4333 (1991).

Reed, "Mechanisms of Apoptosis" *Am. J. Pathol.* 157:1415-1430 (2000).

Regalado, "Turning Off Genes Sheds New Light On How They Work" *The Wall Street Journal*, 4 pages (Aug. 6, 2002).

Rego et al., "Analysis of the Molecular Genetics of Acute Promyelocytic Leukemia in Mouse Models" *Semin. in Hemat.* 38:54-70 (2001).

Robbins et al., "Sensing the danger in RNA" *Nat. Med.* 11(3):250-251 (2005).

Rosenfeld et al., "Adenovirus-Mediated Transfer of a Recombinant a1-Antitrypsin Gene to the Lung Epithelium in Vivo" *Science* 252:431-434 (1991).

Rosenfeld et al., "In Vivo Transfer to the Human Cystic Fibrosis Transmembrane Conductance Regulator Gene to the Airway Epithelium" *Cell* 68:143-155 (1992).

Saison-Behmoaras et al., "Short modified antisense olignucleotides directed against Ha-*ras* point mutation induce selective cleavage of the mRNA and inhibit T24 cells proliferation" *EMBO J.* 10:111-118 (1991).

Scheffer et al., "The drug resistance-related protein LRP is the human major vault protein" *Nat. Med.* 1:578-582 (1995).

Scherr et al., "Quantitative Determination of Lentiviral Vector Particle Numbers by Real-Time PCR" *BioTechniques* 31:520-526 (2001).

Schwarz et al., "Evidence that siRNAs Function as Guides, Not Primers, in the *Drosophila* and Human RNAi Pathways" *Mol. Cell* 10:537-548 (2002).

Secrist et al., Abstract 21, *Program & Abstracts, Tenth International Roundtable, Nucleosides, Nucleotides and their Biological Applications*, Park City, Utah, Sep. 16-20 (1992).

Shannon et al., "Modeling myeloid leukemia tumors suppressor gene inactivation in the mouse" *Semin. Cancer Biol.* 11:191-199 (2001).

Sharp et al., "RNAi and double-strand RNA" *Genes Dev.* 13:139-141 (1999).

Shea et al., "Synthesis hybridization properties and antiviral activity of lipid-oligodeoxynucleotide conjagates" *Nucl. Acids Res.* 18:3777-3783 (1990).

Shi et al., "A CBP/p300 homolog specifies multiple differentiation pathways in *Caenorhabditis elegans*" *Genes Dev.* 12:943-955 (1998).

Sinha, "Large-scale Synthesis. Approaches to Large-scale Synthesis of Oligodeoxynucleotides and their Analogs" *Antisense—From Technology to Therapy*, vol 6, Edited by Reimar Schlingensiepen et al., pp. 29-58 (1997).

Skorski et al., "Suppression of Philadelphia[1] leukemia cell growth in mice by BCR-ABL antisense oligodeoxynucleotide" *Proc. Natl. Acad. Sci. USA* 91:4504-4508 (1994).

Skripkin et al., "Psoralen crosslinking between human immunodeficiency virus type 1 RNA and primer tRNA$_3^{Lys}$" *Nucleic Acids Res.* 24:509-514 (1996).

Sledz et al., "Activation of the interferon system by short-interfering RNAs" *Nat. Cell Biol.* 5(9):834-839 (2003).

Soutschek et al., "Therapeutic silencing of an endogenous gene by systemic administration of modified siRNAs" *Nature* 432:173-178 (2004).

Stetler-Stevenson et al., "Tumor Cell Interactions with the Extracellular Matrix During Invasion and Metastasis" *Annu. Rev. Cell Biol.* 9:541-573 (1993).

Strasser et al., "Apoptosis Signaling" *Annu. Rev. Biochem.* 69:217-245 (2000).

Strauss, "Candidate 'Gene Silencers' Found" *Science* 286:886 (1999).

Svinarchuk et al., "Inhibition of HIV proliferation in MT-4 cells by antisense oligonucleotide conjugated to lipophilic groups" *Biochimie* 75:49-54 (1993).

Thomson et al., "Synthesis and Properties of Diuridine Phosphate Analogues Containign Thio and Amino Modifications" *J. Org. Chem.* 61:6273-6281 (1996).

Timmons et al., "Specific interference by ingested dsRNA" *Nature* 395:854 (1998).

Uhlmann et al., "Antisense Oligonucleotides: A New Therapeutic Principle" *Chemical Reviews* 90:543-584 (1990).

Van Beusechem et al., "Long-term expression of human adenosine deaminase in rhesus monkeys transplanted with retrovirus-infected bone-marrow cells" *Proc. Natl. Acad. Sci. USA* 89:7640-7644 (1992).

Van Etten, "Pathogenesis and treatment of Ph+ leukemia: recent insights from mouse models" *Curr. Opin. Hematol.* 8:224-230 (2001).

Voinnet et al., "Systemic signalling in gene silencing" *Nature* 389:553 (1997).

Wagner, "The state of the art in antisense research" *Nat. Med.* 1:1116-1118 (1995).

Wargelius et al., "Double-Stranded RNA Induces Specific Developmental Defects in Zebrafish Embryos" *Biochem. Biophys. Res. Commun.* 263:156-161 (1999).

Waterhouse et al., "Virus resistance and gene silencing in plants can be induced by simultaneous expression of sense and antisense RNA" *Proc. Natl. Acad. Sci. USA* 95:13959-13964 (1998).

Wess et al., "Early days for RNAi" *BioCentury* 11:A1-A8 (2003).

Wilson et al., "Retrovirus-mediated transduction of adult hepatocytes" *Proc. Natl. Acad. Sci. USA* 85:3014-3018 (1988).

Wong et al., "Modeling Philadelphia chromosome positive leukemias" *Oncogene* 20:5644-5659 (2001).

Yokota, "Tumor progression and metastasis" *Carcinogenesis* 21:497-503 (2000).

Zeng et al., "RNA interference in human cells is restricted to the cytoplasm" *RNA* 8:855-860 (2000).

Zeng et al., "The Fetal Origin of B-Precursor Leukemia in the Eμ-ret Mouse" *Blood* 92:3529-3536 (1988).

Zhao et al., "Double-Stranded RNA Injection Produces Nonspecific Defects in Zebrafish" *Dev. Biol.* 229:215-223 (2001).

Zheng et al., "Activation of the protein kinase PKR by short double-stranded RNAs with single-stranded tails" *RNA* 10:1934-1945 (2004).

Luo et al., "The Gene-Silencing Efficiency of siRNA is Strongly Dependent on the Local Structure of mRNA at the Targeted Region," Biochemical and Biophysical Research Communications, vol. 318 (1):303-10 (2004).

Wacheck, et al., "Small Interfering RNA Targeting Bcl-2 Sensitizes Malignant Melanoma," Oligonucleotides, vol. 13 (5):393-400 (2003).

U.S. Appl. No. 60/117,635, Li et al. (filed Jan. 28, 1999).

Jackson A. L. et al., "Widespread siRNA "off-target" transcript silencing mediated by seed region sequence complementarity," RNA Journal, 12(7): 1179-1187 (2007).

Martinez et al., "Single stranded antisense siRNAs guide target RNA cleavage in RNAi," Cell, 110:563-574 (2002).

Misquitta et al., "Targeted disruption of gene function in Drosophila by RNA interference (RNA-i): A role for nautilus in embryonic somatic muscle formation," PNAS USA, 96:1451-1456 (1999).

Pils, W. et al., "Flexible non-nucleotide linkers as loop replacements in short double helical RNAs," Nucleic Acids Research, 28(9): 1869-1963 (2000).

Zamore et al., "Evidence that siRNAs function as guides not primers in the drosphila and human RNAi pathways," Mol. Cell, 10:537-48 (2002).

Notice of Opposition to German Application No. DE 100 66 235, filed by Pfizer Inc. on Jul. 9, 2008.

List of Documents in Oppositions to German Application No. DE 100 66 235, filed by Silence Therapeutics AG, Sanofi Aventis Deutschland GmbH, and Pfizer Inc.

German Priority Application DE 199 03 713.2 (Filed Jan. 30, 1999).

German Priority Application DE 199 56 568.6 (Filed Nov. 24, 1999).

Declaration of David M. Stalker (Nov. 4, 2008).

Declaration of David Keith Myers (Nov. 7, 2008).

Exhibit 1 of David Keith Myers Declaration (Nov. 7, 2008).

Exhibit 2 of David Keith Myers Declaration (Nov. 7, 2008).

Bruenig, Plant Gene Silencing Regularized, Proc. Natl Acad Science; vol. 95, pp. 13349-13351 (1998).

Cameron et al., Inhibition of Gene Expression by a Short Sense Fragment; Nucleic Acits Research, vol. 19, pp. 469-475 (1991).

Caplan et al., dsRNA-Mediated Gene Silencing in Cultured Drosphila Cells: a Tissue Culture Model for the Analysis of RNA Interference; Gene, vol. 252 pp. 95-105 (2000).

Cotton et al., Ribozyme Mediated Destruction of RNA in vivo; EMBO J., vol. 8, pp. 3861-3866 (1989).

Fire et al., Production of Antisense RNA Leads to Effective and Specific Inhibition of Gene Expression in C. elegans Muscle; Deveopment, vol. 113, pp. 503-514 (1991).

Graessman et al., Inhibition of SV40 Gene Expression by Microinjected Small Antisense RNA and DNA Molecules; Nucleic Acids Research, vol. 19, pp. 53-59 (1991).

Graham, Mapping Transgene Activity in Plants Using Visible Phenotypes; Australian Society for Biochemistry and Molecular Biology Incorporated and Australian Society of Plant Physiologists Incorporated, vol. 28, Abstract SYM-18-06 (1996).

Grierson et al., Does Co-Suppression of Sense Genes in Transgenic Plants Involve Antisense RNA; Trends in Biotechnology, vol. 9, pp. 122-123 (1991).

Guo et al., Par-1 a Gene Required for Establishing Polarity in C. elegans Embryos, Encodes a Putative Ser/Thr Kinase That is Asymmetrically Distributed; Cell vol. 81, pp. 611-620 (1995).

Hunter et al., The Characteristics of Inhibition of Protein Synthesis by Double-Stranded Ribonucleic Acid in Reticulocyte Lysates; J. Biological Chemistry, vol. 250, pp. 409-417 (1975).

Izant et al., Constitutive and Conditional Suppression of Exogenous and Endogenous Genes by Anti-Sense RNA; Science, vol. 229, pp. 345-352 (1985).

Jennings et al., Inhibition of SV40 Replicon Function by Engineered Antisense RNA Transcribed by RNA Polymerase III; EMBO Journal, vol. 6, pp. 3043-3047 (1987).

Jorgensen et al., Silencing of Plant Genes by Homologous Transgenes; AgBiotech News and Information, vol. 4, pp. 265-273 (1992).

Kamio et al.; Nucleotide Sequence of an Incompatibility Region of Mini-Rts1 That Contains Five Direct Repeats; Journal of Bacteriology, vol. 155, pp. 1185-1191 (1983).

Kim et al., Stable Reduction of Thymidine Kinase Activity in Cells Expressing High Levels of Anti-Sense RNA; Cell, vol. 42, pp. 129-138 (1985).

Krieger et al., The Flavr Savr Tomato, an Early Example of RNAi Technology; HortScience, vol. 43, pp. 962-964 (2008).

Lee et al., The C. elegans Heterochronic Gene lin-4 Encodes Small RNAs with Antisense Complementarity to lin-14; Cell, vol. 75, pp. 846-854 (1993).

Maitra et al., HIV-1 TAR RNA Has an Intrinsic Ability to Activate Interferon-Inducible Enzymes; Virology, vol. 204, pp. 823-827 (1994).

Marques et al., A Structural Basis for Discriminating Between Self and Non-Self Double-Stranded RNAs In Mammalian Cells; Nature Biotechnology, vol. 24, pp. 559-565 (2006).

Meister, RNA Interference in the Nucleus; Science, vol. 321, pp. 496-497 (2008).

Mizuno et al., Regulation of Gene Expression by a Small RNA Transcript (micRNA) in *Escherichia coli* K-12); Proc. Japan Acad. vol. 59, pp. 335-338 (1983).

Napoli et al., Introduction of a chimeric Chalcone Synthase Gene into Petunia Results in Reversible Co-Suppression of Homologous Genes in trans; The Plan Cell, vol. 2, pp. 279-289 (1990).

Oates et al., Too Much Interference: Injection of Double-Stranded RNA Has Non-Specific Effects in the Zebrafish Embryo; Developmental Biology, vol. 24, pp. 20-28 (2000).

Pei et al., On the Art of Identifying Effective and Specific siRNAs; Nature Methods, vol. 3, pp. 670-676 (2006).

Pusch et al., Nucleotide Sequence Homology Requirements of HIV-1 Specific Short Hairpin RNA; Nucleic Acids Research; vol. 31, pp. 6444-6449 (2003).

Simons et al., Translational Control of IS10 Transposition; Cell, vol. 34, pp. 683-691 (1983).

Sledz et al., RNA Interference and Double-Stranded RNA Activated Pathways; Biochemical Society Transactions, vol. 32, pp. 956-956 (2004).

Takayama et al., Antisense RNA; Critical Reviews in Biochemistry and Molecular Biology; vol. 25, pp. 155-184 (1991).

Tolun et al.; Cell vol. 24, pp. 687-694 (1981).

Tsutsui et al.; Role of Nine Repeating Sequences of the Mini-F Genome for Expression of F-Specific Incompatibility Phenotype and Copy Number Control; Journal of Bacteriology, vol. 155, pp. 337-344 (1983).

Uhlenbeck, A Small Catalytic Oligoribonucleotide; Nature, vol. 325, pp. 596-600 (1987).

Waterhouse et al., Virus Resistance and Gene Silencing in Plants Can Be Induced by Simultaneous Expression of Sense and Antisense RNA; Proc. Natl. Acad. Science, vol. 95, pp. 13959-13964 (1998).

Guang et al., An Argonaute Transports siRNAs from the Cytoplasm to the Nucleus; Science, vol. 321, pp. 537-541 (2008).

* cited by examiner

SEQUENCE LISTING

```
<160> NUMBER OF SEQ ID NOS: 6

<210> SEQ ID NO 1
<211> LENGTH: 22
<212> TYPE: RNA
<213> ORGANISM: artificial sequence
<220> FEATURE:
```

-continued

```
<223> OTHER INFORMATION: sense strand of dsRNA that is complementary
      to a sequence of the human Bcl-2 gene

<400> SEQUENCE: 1
caggaccucg ccgcugcaga cc                                                  22

<210> SEQ ID NO 2
<211> LENGTH: 24
<212> TYPE: RNA
<213> ORGANISM: artificial sequence
<220> FEATURE:
<223> OTHER INFORMATION: antisense strand of dsRNA that is complementary
      to a sequence of the human Bcl-2 gene

<400> SEQUENCE: 2
ggucugcagc ggcgaggucc uggc                                                24

<210> SEQ ID NO 3
<211> LENGTH: 22
<212> TYPE: RNA
<213> ORGANISM: artificial sequence
<220> FEATURE:
<223> OTHER INFORMATION: sense strand of dsRNA that is complementary to
      a sequence of thehuman Bcl-2 gene

<400> SEQUENCE: 3
gccuuugugg aacuguacgg cc                                                  22

<210> SEQ ID NO 4
<211> LENGTH: 24
<212> TYPE: RNA
<213> ORGANISM: artificial sequence
<220> FEATURE:
<223> OTHER INFORMATION: antisense strand of dsRNA that is complementary
      to a sequence of the human Bcl-2 gene

<400> SEQUENCE: 4
ggccguacag uuccacaaag gcau                                                24

<210> SEQ ID NO 5
<211> LENGTH: 22
<212> TYPE: RNA
<213> ORGANISM: artificial sequence
<220> FEATURE:
<223> OTHER INFORMATION: sense strand of dsRNA that is complementary to
      a sequence of theneomycin resistance gene

<400> SEQUENCE: 5
caaggaugag gaucguuucg ca                                                  22

<210> SEQ ID NO 6
<211> LENGTH: 23
<212> TYPE: RNA
<213> ORGANISM: artificial sequence
<220> FEATURE:
<223> OTHER INFORMATION: antisense strand of dsRNA that is complementary
      to a sequence of the neomycin resistance gene

<400> SEQUENCE: 6
gcgaaacgau ccucauccug ucu                                                 23
```

COMPOSITIONS AND METHODS FOR INHIBITING EXPRESSION OF ANTI-APOPTOTIC GENES

RELATED APPLICATIONS

This application is a continuation-in-part of International Application No. PCT/EP02/00151, which designated the United States and was filed on Jan. 9, 2002, which claims the benefit of German Patent No. 101 00 586.5, filed on Jan. 9, 2001. The entire teachings of the above application(s) are incorporated herein by reference.

FIELD OF THE INVENTION

This invention relates to double-stranded ribonucleic acid (dsRNA), and its use in mediating RNA interference to inhibit the expression of an anti-apoptotic target gene, such as a Bcl gene.

BACKGROUND OF THE INVENTION

Many diseases, incuding cancers, arise from the abnormal expression or activity of a particular gene, a group of genes, or a mutant form of protein. The therapeutic benefits of being able to selectively silence the expression of these genes is obvious.

A number of therapeutic agents designed to inhibit expression of a target gene have been developed, including antisense ribonucleic acid (RNA) (see, e.g., Skorski, T. et al., *Proc. Natl. Acad. Sci. USA* (1994) 91:4504-4508) and hammerhead-based ribozymes (see, e.g., James, H. A, and I. Gibson, *Blood* (1998) 91:371). However, both of these agents have inherent limitations. Antisense approaches, using either single-stranded RNA or DNA, act in a 1:1 stoichiometric relationship and thus have low efficacy (Skorski et al., supra). Hammerhead ribozymes, which because of their catalytic activity can degrade a higher number of target molecules, have been used to overcome the stoichiometry problem associated with antisense RNA. However, hammerhead ribozymes require specific nucleotide sequences in the target gene, which are not always present.

More recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of a target gene in *C. elegans*. dsRNA has also been shown to degrade target RNA in other organisms, including plants (see, e.g., WO 99/53050, Waterhouse et al.; and WO 99/61631, Heifetz et al.), *Drosophilia* (see, e.g., Yang, D., et al., *Curr. Biol.* (2000) 10:1191-1200), and mammals (see WO 00/44895, Limmer; and DE 101 00 586.5, Kruetzer et al.).

In RNA interference, the RNAse III Dicer processes dsRNA into small interfering RNAs (siRNA) of approximately 22 nucleotides, which serve as guide sequences to induce target-specific mRNA cleavage by an RNA-induced silencing complex RISC (Hammond, S. M., et al., *Nature* (2000) 404:293-296). In other words, RNAi involves a catalytic-type reaction whereby new siRNAs are generated through successive cleavage of long dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

Gautschi et al. report that the expression levels of the anti-apoptotic proteins Bcl-1 and Bcl-xL are elevated during the development and progression of tumors (Gautschi, O., et al., *J. Natl. Cancer Inst.* (2001) 93:463-471). Tumor growth (but not size) was reduced by approximately 50-60% in nude mice treated with a combination of single-stranded antisense oligoribonucleotides targeted to Bcl-2 and Bcl-xL genes. However, because of the 1:1 stoichiometric relationship and thus low efficiency of antisense RNA, the anti-Bcl treatment required 20 milligrams of antisense RNA per kilogram body weight of recipient mouse per day. Producing therapeutically sufficient amounts of RNA is not only expensive, but single-stranded antisense RNA is highly susceptible to degradation by serum proteases, thus resulting in a short in vivo half-life.

Despite significant advances in the field, there remains a need for an agent that can selectively and efficiently silence a target gene using the cell's own RNAi machinery. More specifically, an agent that has both high biological activity and in vivo stability, and that can effectively inhibit expression of a target anti-apoptotic gene at a low dose, would be highly desirable. Compositions comprising such agents would be useful for treating diseases caused by the expression of these genes.

SUMMARY OF THE INVENTION

The present invention discloses double-stranded ribonucleic acid (dsRNA), as well as compositions and methods for inhibiting the expression of a target gene, such as an anti-apoptotic gene, in a cell using the dsRNA. The present invention also discloses compositions and methods for treating diseases caused by the expression of a target anti-apoptotic gene (e.g., a Bcl gene). The dsRNA of the invention comprises an RNA strand (the complementary strand) having a region which is less than 25 nucleotides in length and is complementary to at least a portion of an RNA transcript of an anti-apoptotic target gene, such as Bcl-2, Bcl-w, or Bcl-xL.

In one aspect, the invention relates to a double-stranded ribonucleic acid (dsRNA) for inhibiting the expression of an anti-apoptotic gene in a cell. The dsRNA comprises a complementary RNA strand having a complementary nucleotide sequence which is complementary to at least a part of the anti-apoptotic gene, and which is less than 25 nucleotides in length. The dsRNA may further comprise a sense RNA strand, and at least one of the RNA strands comprises a nucleotide overhang of 1 to 4 nucleotides, preferably 2 or 3 nucleotides in length. In a preferred embodiment, the nucleotide overhang is on the 3'-terminus of the complementary RNA strand, and the 5'-end is blunt. The complementary RNA strand and sense RNA strand have a region of complementarilty, which may be 19 to 24 nucleotides, preferably 21 to 24 nucleotides, and most preferably 22 nucleotides in length. The complementary RNA strand may be less than 30, preferably less than 25, and most preferably 21 to 24 nucleotides in length. In one embodiment, the dsRNA may have at least one, preferably two, linkers between the complementary RNA strand and the sense RNA strand, such as a chemical linker. The chemical linker may be a hexaethylene glycol linker, apoly-(oxyphosphinico-oxy-1,3-propandiol) linker, or an oligoethyleneglycol linker. The anti-apoptotic gene may be a Bcl gene, such as Bcl-2, Bcl-w, or Bcl-xL. In one embodiments, both the complementary RNA strand and the sense RNA strand comprise the sequence of SEQ ID NO:2. In another embodiment, the complementary RNA strand comprises the sequence of SEQ ID NO:4, and the sense RNA strand comprises the sequence of SEQ ID NO:3. The cell may be a pancreatic carcinoma cell.

In another aspect, the invention relates to a method for inhibiting the expression of an anti-apoptotic gene in a cell. The method comprises introducing into the cell a dsRNA, as described above, then maintaining the cell for a time sufficient to obtain degradation of the mRNA transcript of the anti-apoptotic gene. The cell may be a pancreatic carcinoma cell.

In yet another aspect, the invention relates to a pharmaceutical composition for inhibiting the expression of an anti-apoptic gene in an organism. The pharmaceutical composition comprises a dsRNA, as described above, and a pharmaceutically acceptable carrier. The anti-apoptotic gene may be a Bcl gene, such Bcl-2, Bcl-w, or Bcl-xL. The cell may be a pancreatic carcinoma cell, and the organism may be a mammal, such as a human. The dosage unit of dsRNA in the pharmaceutical composition may be less than 5 milligram (mg) of dsRNA, preferably in a range of 0.01 to 2.5 milligrams (mg), more preferably 0.1 to 200 micrograms (μg), even more preferably 0.1 to 100 μg, and most preferably less than 25 μg per kilogram body weight of the mammal. The pharmaceutically acceptable carrier may be an aqueous solution, such phosphate buffered saline. The pharmaceutically acceptable carrier may comprise a micellar structure, such as a liposome, capsid, capsoid, polymeric nanocapsule, or polymeric microcapsule. In a preferred embodiment, the micellar structure is a liposome. The pharmaceutical composition may be formulated to be administered by inhalation, infusion, injection, or orally, preferably by intravenous or intraperitoneal injection.

In still another aspect, the invention relates to method for treating a disease caused by the expression of an anti-apoptotic gene in a mammal. The method comprises administering a pharmaceutical composition, as described above, to the mammal. The disease to be treated may be a pancreatic carcinoma.

The details of once or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
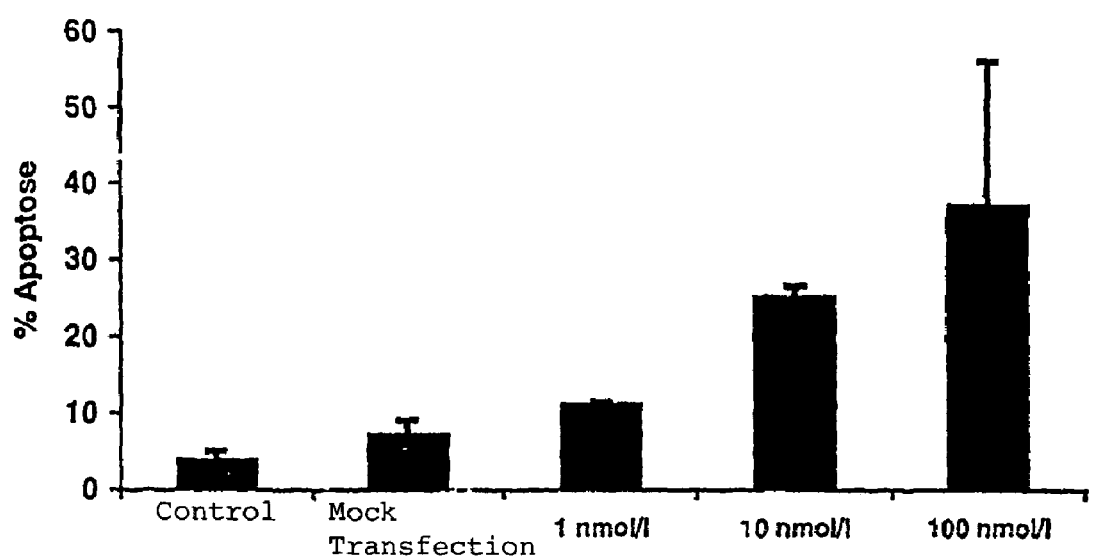
FIG. 1 shows the apoptosis rate (percent) of human pancreatic YAP C cancer cells, 120 hours after transfection with dsRNA 1 that is complementary to a first sequence of the human Bcl-2 gene.

The present invention discloses double-stranded ribonucleic acid (dsRNA), as well as compositions and methods for inhibiting the expression of a target gene in a cell using the dsRNA. The present invention also discloses compositions and methods for treating diseases in organisms caused by the expression of an anti-apoptotic gene using dsRNA. dsRNA directs the sequence-specific degradation of mRNA through a process known as RNA interference (RNAi). The process occurs in a wide variety of organisms, including mammals and other vertebrates.

The dsRNA of the invention comprises an RNA strand (the complementary strand) having a region which is less than 25 nucleotides in length and is complementary to at least a portion of an RNA transcript of an anti-apoptotic target gene, such as Bcl-2, Bcl-w, or Bcl-xL. The use of these dsRNAs enables the targeted degradation of mRNAs of genes that are implicated in uncontrolled cell or tissue growth. Using cell-based assays, the present inventors have demonstrated that very low dosages of these dsRNA can specifically and efficiently mediate RNAi, resulting in significant inhibition of expression of the target gene(s). Not only are lower dosages of dsRNA required as compared to traditional antisense RNA, but dsRNA affects apoptosis to such an extent that there is a noticeable reduction in both tumor size and number of tumor cells. Thus, the present invention encompasses these dsRNAs and compositions comprising dsRNA and their use for specifically silencing genes whose protein products either inhibit or prevent apoptosis in tumor cells. Moreover, the dsRNAs of the invention have no apparent effect on neighboring normal cells. Thus, the methods and compositions of the present invention comprising these dsRNAs are useful for treating cellular proliferative and/or differentiation disorders, such as cancer.

The following detailed description discloses how to make and use the dsRNA and compositions containing dsRNA to inhibit the expression of target anti-apoptotic genes, as well as compositions and methods for treating diseases and disorders caused by the expression of these genes. The pharmaceutical compositions of the present invention comprise a dsRNA having an RNA strand comprising a complementary region which is less than 25 nucleotides in length and is complementary to at least a portion of an RNA transcript of an anti-apoptotic target gene, together with a pharmaceutically acceptable carrier. The anti-apoptotic gene may be a member of the Bcl-2 family, such as Bcl-2, Bcl-w, or Bcl-xL. The pharmaceutical composition may comprise a combination of dsRNAs having regions complementary to a plurality of anti-apoptotic genes, for example a combination of Bcl-2, Bcl-xL, and/or Bcl-w. Since many types of tumor cells are known to express multiple anti-apoptotic genes, compositions comprising a combination of dsRNAs are particularly effective at inhibiting the development and/or growth of tumor cells.

Accordingly, certain aspects of the present invention relate to pharmaceutical compositions comprising the dsRNA of the present invention together with a pharmaceutically acceptable carrier, methods of using the compositions to inhibit expression of a target anti-apoptotic gene, and methods of using the pharmaceutical compositions to treat diseases caused by expression of at least one of these anti-apoptotic genes.

I. Definitions

For convenience, the meaning of certain terms and phrases used in the specification, examples, and appended claims, are provided below.

As used herein, "target gene" refers to a section of a DNA strand of a double-stranded DNA that is complementary to a section of a DNA strand, including all transcribed regions, that serves as a matrix for transcription. A target gene, usually the sense strand, is a gene whose expression is to be selectively inhibited or silenced through RNA interference. As used herein, the term "target gene" specifically encompasses any cellular gene or gene fragment whose expression or activity is associated with the inhibition or prevention of apoptosis. For example, the target gene may be a gene from the Bcl-2 gene family, such as Bcl-2, Bcl-w, and/or Bcl-xL.

The term "complementary RNA strand" (also referred to herein as the "antisense strand") refers to the strand of a dsRNA which is complementary to an mRNA transcript that is formed during expression of the target gene, or its processing products. As used herein, the term "complementary nucleotide sequence" refers to the region on the complementary RNA strand that is complementary to an mRNA transcript of a portion of the target gene. "dsRNA" refers to a ribonucleic acid molecule having a duplex structure comprising two complementary and anti-parallel nucleic acid strands. Not all nucleotides of a dsRNA must exhibit Watson-Crick base pairs; the two RNA strands may be substantially complementary (i.e., having no more than one or two nucleotide mismatches). The maximum number of base pairs is the number of nucleotides in the shortest strand of the dsRNA. The RNA strands may have the same or a different number of nucleotides. The dsRNA is less than 30, preferably less than 25, and most preferably between 21 and 24 nucleotides in length. dsRNAs of this length are particularly efficient in inhibiting the expression of the target anti-apoptotic gene. "Introducing into" means uptake or absorption in the cell, as is understood by those skilled in the art. Absorption or uptake of dsRNA can occur through cellular processes, or by auxiliary agents or devices. For example, for in vivo delivery, dsRNA can be injected into a tissue site or administered systemically. In vitro delivery includes methods known in the art such as electroporation and lipofection.

As used herein, a "nucleotide overhang" refers to the unpaired nucleotide or nucleotides that protrude from the duplex structure when a 3'-end of one RNA strand extends beyond the 5'-end of the other strand, or vice versa.

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M. Stockton Press, New York (1991)). Methods commonly employed to determine identity between sequences include, for example, those disclosed in Carillo, H., and Lipman, D., *SIAM J. Applied Math.* (1988) 48:1073. "Substantially identical," as used herein, means there is a very high degree of homology (preferably 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a dsRNA molecule has been introduced by means of recombinant DNA techniques.

II. Double-stranded Ribonucleic Acid (dsRNA)

In one embodiment, the invention relates to a double-stranded ribonucleic acid (dsRNA) having a nucleotide sequence which is substantially identical to at least a portion of a target gene. The dsRNA comprises two RNA strands that are sufficiently complementary to hybridize to form the duplex structure. One strand of the dsRNA comprises the nucleotide sequence that is substantially identical to a portion of the target gene (the "sense" strand), and the other strand (the "complementary" or "antisense" strand) comprises a sequence that is complementary to an RNA tanscript of the target gene. The complementary region is less between 19 and 24, preferably between 21 and 23, and most preferably 22 nucleotides in length. The dsRNA is less than 30 nucleotides, preferably less than 25 nucleotides, and most preferably between 21 and 24 nucleotides in length. The dsRNA can be synthesized by standard methods known in the art, e.g., by use of an automated DNA synthesizer, such as are commercially available from Biosearch, Applied Biosystems, Inc. In a preferred embodiment, the target gene is a member of the Bcl-2 family, e.g., Bcl-2, Bcl-2, or Bcl-xL. In specific embodiments, the complementary (antisense) RNA strand of the dsRNA comprises the sequence set forth in SEQ ID NO:2 and the second (sense) RNA strand comprises the sequence set forth in SEQ ID NO:1; or the complementary (antisense) RNA strand of the dsRNA comprises the sequence set forth in SEQ ID NO:4 and the second (sense) RNA strand comprises the sequence set forth in SEQ ID NO:3.

In one embodiment, at least one end of the dsRNA has a single-stranded nucleotide overhang of 1 to 4, preferably 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without effecting its overall stability. dsRNA having only one overhang has proven particularly stable and effective in vivo, as well as in a variety of cells, cell culture mediums, blood, and serum. Preferably, the single-stranded overhang is located at the 3'-terminal end of the complementary (antisense) RNA strand or, alternatively, at the 3'-terminal end of the second (sense) strand. The dsRNA may also have a blunt end, preferably located at the 5'-end of the complementary (antisense) strand. Such dsRNAs have improved stability and inhibitory activity, thus allowing administration at low dosages, i.e., less than 5 mg/kg body weight of the recipient per day. Preferably, the complementary strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified for improved stability, i.e., enhanced resistance to degradation and/or strand dissociation. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. In one embodiment, the linker is a hexa-ethylene glycol linker. In this case, the dsRNAs are produced by solid phase synthesis and the hexa-ethylene glycol linker is incorporated according to standard methods (e.g., Williams, D. J., and K. B. Hall, *Biochem.* (1996) 35:14665-14670). In a preferred embodiment, the 5'-end of the complementary (antisense) RNA strand and the 3'-end of the second (sense) RNA strand are chemically linked via a hexa-ethylene glycol linker.

III. Pharmaceutical Compositions Comprising dsRNA

In one embodiment, the invention relates to a pharmaceutical composition comprising a dsRNA, as described in the preceding section, and a pharmaceutically acceptable carrier, as described below. The pharmaceutical composition comprising the dsRNA is useful for treating a disease or disorder associated with the expression or activity of an anti-apoptotic gene.

In another embodiment, the invention relates to a pharmaceutical composition comprising at least two dsRNAs, designed to target different anti-apoptotic genes, and a pharmaceutically acceptable carrier. The anti-apoptotic genes may be members of the Bcl-2 family, such as Bcl-2, Bcl-w, or Bcl-xL. Due to the targeting of mRNA of multiple anti-apoptotic genes, pharmaceutical compositions comprising a plurality of dsRNAs may provide improved efficiency of treatment as compared to compositions comprising a single dsRNA, at least in tumor cells expressing these multiple genes. In this embodiment, the individual dsRNAs are prepared as described in the preceding section, which is incorporated by reference herein. One dsRNA may have a nucleotide sequence which is substantially identical to at least a portion of one anti-apoptotic gene; additional dsRNAs are prepared, each of which has a nucleotide sequence that is substantially identical to a portion of a different anti-apoptotic gene. For example, one dsRNA may have a nucleotide sequence that is substantially identical to a Bcl-2 gene, another dsRNA may have a nucleotide sequence that is substantially identical to a Bcl-xL gene, and yet another dsRNA may have a nucleotide sequence that is substantially identical to a Bcl-w gene. The multiple dsRNAs may be combined in the same pharmaceutical composition, or formulated separately. If formulated individually, the compositions containing the separate dsRNAs may comprise the same or different carriers, and may be administered using the same or different routes of administration. Moreover, the pharmaceutical compositions comprising the individual dsRNAs may be administered substantially simultaneously, sequentially, or at preset intervals throughout the day or treatment period. Although the foregoing description relates to target genes from the Bcl-2 family, the present invention encompasses any gene or combination of genes that have an inhibitory or preventive effect on apoptosis.

The pharmaceutical compositions of the present invention are administered in dosages sufficient to inhibit expression of the target gene. The present inventors have found that, because of their improved efficiency, compositions comprising the dsRNA of the invention can be administered at surprisingly low dosages. A maximum dosage of 5 mg dsRNA per kilogram body weight of recipient per day is sufficient to inhibit or completely suppress expression of the target gene.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases. For example, mouse models are available for hematopoietic malignancies such as leukemias, lymphomas and acute myelogenous leukemia. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov), as well as the NCI-MMHCC mouse repository. Examples of the genetic tools that are currently available for the modeling of leukemia and lymphomas in mice, and which are useful in practicing the present invention, are described in the following references: Maru, Y., *Int. J. Hematol.* (2001) 73:308-322; Pandolfi, P. P., *Oncogene* (2001) 20:5726-5735; Pollock, J. L., et al., *Curr. Opin. Hematol.* (2001) 8:206-211; Rego, E. M., et al., *Semin. in Hemat.* (2001) 38:4-70; Shannon, K. M., et al. (2001) Modeling myeloid leukemia tumors suppressor gene inactivation in the mouse, *Semin. Cancer Biol.* 11, 191-200; Van Etten, R. A., (2001) *Curr. Opin. Hematol.* 8, 224-230; Wong, S., et al. (2001) *Oncogene* 20, 5644-5659; Phillips J A., *Cancer Res.* (2000) 52(2):437-43; Harris, A. W., et al, *J. Exp. Med.* (1988) 167(2):353-71; Zeng X X et al., *Blood.* (1988) 92(10):3529-36; Eriksson, B., et al., *Exp. Hematol.* (1999) 27(4):682-8; and Kovalchuk, A. et al., *J. Exp. Med.* (2000) 192(8):1183-90. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

For oral administration, the dsRNAs useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the target gene. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits expression of the target gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

In one embodiment, the encapsulated formulation comprises a viral coat protein. In this embodiment, the dsRNA may be bound to, associated with, or enclosed by at least one viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs useful according to the invention can be administered in combination with other known agents effective in treatment of diseases. In any event, the administering physician can adjust the amount and timing of dsRNA administration on the basis of results observed using standard measures of efficacy known in the art or described herein.

For oral administration, the dsRNAs useful in the invention will generally be provided in the form of tablets or capsules, as a powder or granules, or as an aqueous solution or suspension.

IV. Methods for Treating Diseases Caused by Expression of an Anti-apoptotic Gene.

In one embodiment, the invention relates to a method for treating a subject having a disease or at risk of developing a disease caused by the expression of an anti-apoptotic target gene. In this embodiment, the dsRNA can act as novel therapeutic agents for controlling one or more of cellular proliferative and/or differentiative disorders. The method comprises administering a pharmaceutical composition of the invention to the patient (e.g., human), such that expression of the target gene is silenced. Because of their high specificity, the dsRNAs of the present invention specifically target mRNAs of target genes of diseased cells and tissues, as described below, and at surprisingly low dosages.

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, e.g. aurora kinase, may be brought into contact with or introduced into a cancerous cell or tumor gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of pancreas, prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoietic origin, e.g., arising from myeloid, lymphoid or erythroid lineages, or precursor cells thereof.

Examples of genes which can be targeted for treatment include, without limitation, an oncogene (Hanahan, D. and R. A. Weinberg, *Cell* (2000) 100:57; and Yokota, J., *Carcinogenesis* (2000) 21(3):497-503); genes of proteins that are involved in metastasizing and/or invasive processes (Boyd, D., *Cancer Metastasis Rev.* (1996) 15(1):77-89; Yokota, J., *Carcinogenesis* (2000) 21(3):497-503); genes of proteases as well as of molecules that regulate apoptosis and the cell cycle (Matrisian, L. M., *Curr. Biol.* (1999) 9(20):R776-8; Krepela, E., *Neoplasma* (2001) 48(5):332-49; Basbaum and Werb, *Curr. Opin. Cell Biol.* (1996) 8:731-738; Birkedal-Hansen, et al., *Crit. Rev. Oral Biol. Med.* (1993) 4:197-250; Mignatti and Rifkin, *Physiol. Rev.* (1993) 73:161-195; Stetler-Stevenson, et al., *Annu. Rev. Cell Biol.* (1993) 9:541-573; Brinkerhoff, E., and L. M. Matrisan, *Nature Reviews* (2002) 3:207-214; Strasser, A., et al., *Annu. Rev. Biochem.* (2000) 69:217-45; Chao, D. T. and S. J. Korsmeyer, *Annu. Rev. Immunol.* (1998) 16:395-419; Mullauer, L., et al., *Mutat. Res.* (2001) 488(3): 211-31; Fotedar, R., et al., *Prog. Cell Cycle Res.* (1996) 2:147-63; Reed, J. C., *Am. J. Pathol.* (2000) 157(5):1415-30; D'Ari, R., *Bioassays* (2001) 23(7):563-5); genes that express the EGF receptor; Mendelsohn, J. and J. Baselga, *Oncogene* (2000) 19(56):6550-65; Normanno, N., et al., *Front. Biosci.* (2001) 6:D685-707); and the multi-drug resistance 1 gene, MDR1 gene (Childs, S., and V. Ling, *Imp. Adv. Oncol.* (1994) 21-36).

In one embodiment, a pharmaceutical compositions comprising dsRNA is used to inhibit the expression of the multi-drug resistance 1 gene ("MDR1"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oncol.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258:1650-1654) and lung resistance protein (LRP) (Scheffer, G. L., et al., *Nat. Med.* (1995)1:578-582) and mutation of DNA topoisomerase II (Beck, W. T., *J. Natl. Cancer Inst.* (1989) 81:1683-1685) also may render MDR.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

V. Methods for Inhibiting Expression of an Anti-apoptotic Gene

In yet another aspect, the invention relates to a method for inhibiting the expression of an anti-apoptotic gene in an organism. The method comprises administering a composition of the invention to the organism such that expression of the target anti-apoptotic gene is silenced. The organism may be an animal or a plant. Because of their high specificity, the dsRNAs of the present invention specifically target RNAs (primary or processed) of target anti-apoptotic genes, and at surprisingly low dosages. Compositions and methods for inhibiting the expression of these target genes using dsRNAs can be performed as described elsewhere herein.

In one embodiment, the comprises administering a composition comprising a dsRNA, wherein the dsRNA comprises a nucleotide sequence which is complementary to at least a part of an RNA transcript of the target anti-apoptotic gene of the organism to be treated. When the organism to be treated is a mammal, such as a human, the composition may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the compositions are administered by intravenous or intraparenteral infusion or injection.

The methods for inhibiting the expression of a target gene can be applied to any gene or group of genes that have a direct or indirect inhibitory affect on apoptosis. Examples of human genes which can be targeted for silencing according to the methods of the present invention include, without limitation, an oncogene; a gene that expresses molecules that induce angiogenesis; genes of proteins that are involved in metastasizing and/or invasive processes; and genes of proteases as well as of molecules that regulate apoptosis and the cell cycle. In a preferred embodiment, the tumor disease to be treated is a pancreatic carcinoma. There is no known treatment for pancreatic cancer, which currently has a survival rate of approximately 3%, the lowest of all carcinomas.

The methods for inhibition the expression of a target gene can also be applied to any plant anti-apoptotic gene one wishes to silence, thereby specifically inhibiting its expression.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Inhibition of Bcl-2 Gene Expression by RNA Interference

The cells of the human pancreatic Yap C cancer line (German Microorganism and Cell Culture Collection, Braunschweig, (No. ACC 382)), were cultured at 37° C., 5% $CO_2$ in RPMI 1640 medium (Biochrom Corp., Berlin) with 10% fetal calf serum (FCS) and 1% penicillin/streptomycin. Human skin fibroblasts were cultured under the same conditions in Dulbecco's MEM with 10% FCS and 1% penicillin/streptomycin. The double-stranded oligoribonucleotides used for transfection have the following sequences, designated as SEQ ID NO:1 to SEQ ID No:6 in the sequence protocol:

dsRNA 1, which is complementary to a first sequence of the human Bcl-2 gene:
S2: 5'-cag gac cuc gcc gcu gca gac c-3' (SEQ ID NO:1)
S1: 3'-cg guc cug gag egg cga cgu cug g-5' (SEQ ID NO:2)

dsRNA 2, which is complementary to a second sequence of the human Bcl-2 gene:
S2: 5'-g ccu uug ugg aac ugu acg gcc-3' (SEQ ID NO:3)
S1: 3'-uac gga aac acc uug aca ugc cgg-5' (SEQ ID NO:4)

dsRNA 3, which is complementary to a sequence of the neomycin resistance gene:
S2: 5'-c aag gau gag gau cgu uuc gca-3' (SEQ ID NO:5)
S1: 3'-ucu guc cua cuc cua gca aag cg-5' (SEQ ID NO:6)

Transfection was carried out in a 6-well plate with oligofectamine (Invitrogen Corp., Karlsruhe). 250,000 cells were placed in each well. Transfection of the double-stranded oligoribonucleotides was carried out in accordance with the oligofectamine protocol recommended by Invitrogen (the data relate to 1 well of a 6-well plate): 10 µl of the double-stranded oligoribonucleotides (0.1-10 µM) were diluted with 175 µl cell culture medium without additives. 3 µl oligofectamine were diluted with 12 µl cell culture medium without additives, and incubated for 10 minutes at room temperature. The diluted oligofectamine was then added to the diluted double-stranded oligoribonucleotides, mixed, and incubated for 20 minutes at room temperature. During this time, the cells to be transfected were washed once with cell culture medium without additives, and 800 µl of fresh cell culture medium was added so that the transfection end volume was 1000 µl. This results in a double-stranded oligoribonucleotide end concentration of 1-100 µM. The transfection media was incubated with the cells for four hours at 37° C. 500 µl of cell culture medium with 30% FCS were then placed in each well, i.e. final concentration of FCS was 10%. The cells were then incubated for 120 hours at 37° C., at which time they were washed with phosphate buffered saline (PBS), trypsinized and centrifuged for 10 minutes at 100 g. The supernatant fluid was discarded, and the pellet was incubated in the dark with hypotonic propidium iodide solution for 30 minutes at 4° C. The pelletted cells were then analyzed by flow cytometry using a FACSCalibur fluorescence-activated cell sorter (BD GmbH, Heidelberg).

Figure 2:
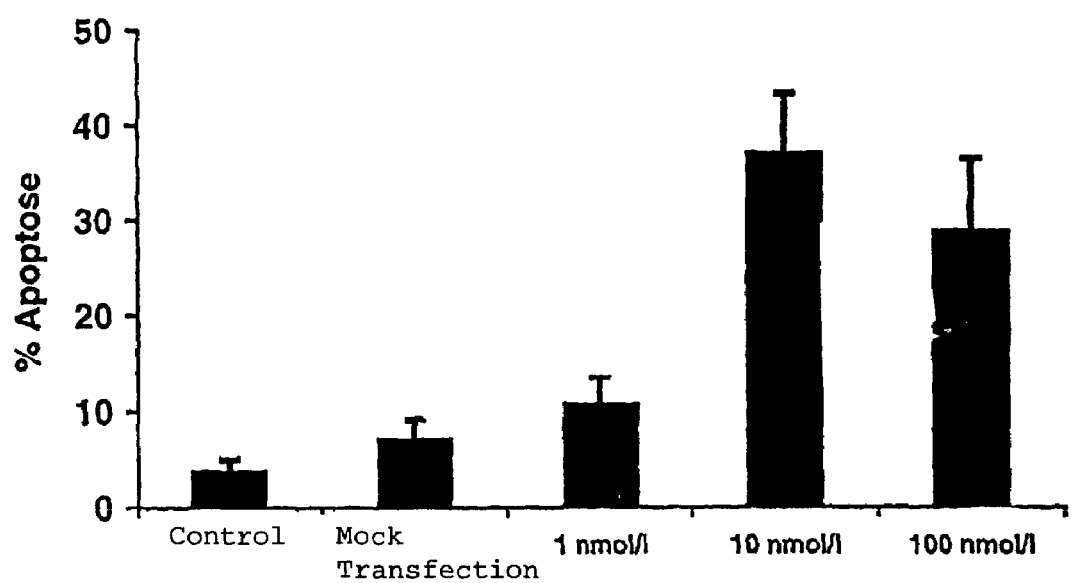
FIG. 2 shows the apoptosis rate (percent) of YAP C cells, 120 hours after transfection with dsRNA 2 that is complementary to a first sequence of the human Bcl-2 gene.
Figure 3:
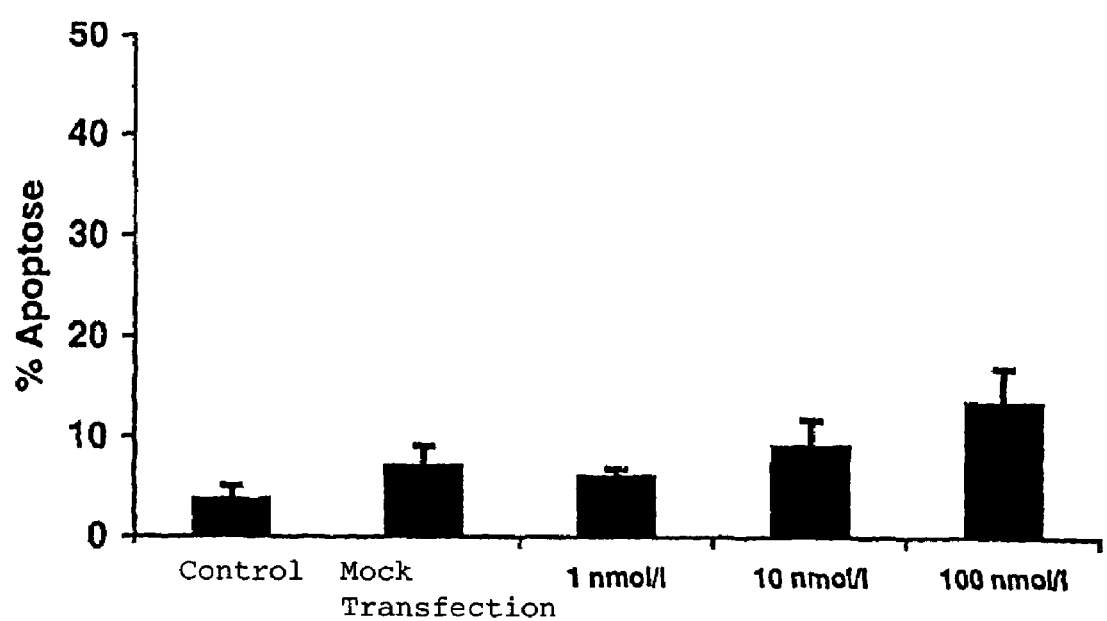
FIG. 3 shows the apoptosis rate (percent) of YAP C cells, 120 hours after transfection with dsRNA 3 that is complementary to a sequence of the neomycin resistance gene.

Both the double-stranded oligoribonucleotides dsRNA 1 and dsRNA 2 decreased the inhibition of apoptosis mediated by Bcl-2 in the human pancreatic cancer cells studied. No additional stimulation of apoptosis was required to induce or initiate apoptosis. The apoptosis rate rose independent of incubation time. FIG. 1 shows the result achieved with dsRNA 1 and FIG. 2 that with dsRNA 2. Whereas untreated YAP C control cells and cells with which the described methods of transfection were carried out without double-stranded oligoribonucleotides (mock-transfected cells) showed an apoptosis rate of only 3.8% and 7.1% after 120 hours incubation, the apoptosis rate achieved with 100 nM dsRNA rose to 37.2% for transfection with dsRNA 1 and 28.9% for transfection with dsRNA 2. Control transfection with dsRNA 3 led to a maximum apoptosis rate of 13.5%. This represents no significant increase when compared to mock-transfected cells, and proves the sequence specificity of the action of the dsRNA 1 and dsRNA 2. As a control, skin fibroblasts were transfected as non-transformed cells with dsRNA 1 and dsRNA 2. After 120 hours, these cells showed no significant increase in apoptosis rate.

Example 2

Treatment of a Pancreatic Cancer Patient with dsRNA 1 and 2

In this Example, dsRNA 1 and 2 are injected into a pancreatic cancer patient and shown to specifically inhibit Bcl-2 gene expression.

Synthesis and Preparation of dsRNAs dsRNA 1 and 2 directed against the Bcl-2 gene are chemically synthesized with or without a hexaethylene glycol linker. Oligoribonucleotides are synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM Tris, 10 mM $NaClO_4$, pH 6.8, 10% acetonitrile; the high-salt buffer was: 20 mM Tris, 400 mM NaClO4, pH 6.8, 10% acetonitrile. flow rate: 3 ml/min). Formation of double stranded dsRNAs is then achieved by heating a stoichiometric mixture of the individual complementary strands (10 μM) in 10 mM sodium phosphate buffer, pH 6.8, 100 mM NaCl, to 80-90° C., with subsequent slow cooling to room temperature over 6 hours.

In addition, dsRNA molecules with linkers may be produced by solid phase synthesis and addition of hexaethylene glycol as a non-nucleotide linker (Jeremy, D., et al., *Biochem.* (1996), 35:14665-14670). A hexaethylene glycol linker phosphoramidite (Chruachem Ltd, Todd Campus, West of Scotland Science Park, Acre Road, Glasgow, G20 OUA, Scotland, UK) is coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite is comparable to the incorporation of nucleoside phosphoramidites.

dsRNA Administration and Dosage

The present example provides for pharmaceutical compositions for the treatment of human pancreatic cancer patients comprising a therapeutically effective amount of a dsRNA 1 and dsRNA 2 as disclosed herein, in combination with a pharmaceutically acceptable carrier or excipient. dsRNAs useful according to the invention may be formulated for oral or parenteral administration. The pharmaceutical compositions may be administered in any effective, convenient manner including, for instance, administration by topical, oral, anal, vaginal, intravenous, intraperitoneal, intramuscular, subcutaneous, intranasal or intradermal routes among others. One of skill in the art can readily prepare dsRNAs for injection using such carriers that include, but are not limited to, saline, buffered saline, dextrose, water, glycerol, ethanol, and combinations thereof. Additional examples of suitable carriers are found in standard pharmaceutical texts, e.g. "Remington's Pharmaceutical Sciences", 16th edition, Mack Publishing Company, Easton, Pa. (1980).

RNA Purification and Analysis

Efficacy of the dsRNA treatment is determined at defined intervals after the initiation of treatment using real time PCR on total RNA extracted from tissue biopsies. Cytoplasmic RNA from tissue biopsies, taken prior to and during treatment, is purified with the help of the RNeasy Kit (Qiagen, Hilden) and Bcl-2 mRNA levels are quantitated by real time RT-PCR as described previously (Eder, M., et al., *Leukemia* (1999) 13:1383-1389; Scherr, M., et al., *BioTechniques* (2001) 31:520-526). Analysis of Bcl-2 mRNA levels before and during treatment by real time PCR, provides the attending physician with a rapid and accurate assessment of treatment efficacy as well as the opportunity to modify the treatment regimen in response to the patient's symptoms and disease progression.

Example 3 dsRNA Expression Vectors

In another aspect of the invention, Bcl-2 specific dsRNA molecules that interact with Bcl-2 target RNA molecules and modulate Bcl-2 gene expression activity are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are preferably DNA plasmids or viral vectors. dsRNA expressing viral vectors can be constructed based on, but not limited to, adeno-associated virus (for a review, see Muzyczka, et al., *Curr. Topics Micro. Immunol.* (1992) 158:97-129)); adenovirus (see, for example, Berkner, et al., BioTechniques (1998) 6:616), Rosenfeld et al. (1991, Science 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Cornette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D 1-thiogalactopyranoside (EPTG). A person skilled in the art would be able to choose the appropriate regulatory/promoter sequence based on the intended use of the dsRNA transgene.

Preferably, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

DsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single target gene or multiple target genes over a period of a week or more are also contemplated by the present invention. Successful introduction of the vectors of the invention into host cells can be monitored using various known methods. For example, transient transfection can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The dsRNA 1 and 2 molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Example 4

Method of Determining an Effective Dose of a dsRNA

A therapeutically effective amount of a composition containing a sequence that encodes Bcl-2 specific dsRNA, (i.e., an effective dosage), is an amount that inhibits expression of the polypeptide encoded by the Bcl-2 target gene by at least 10 percent. Higher percentages of inhibition, e.g., 15, 20, 30, 40, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. In some cases transient expression of the dsRNA may be desired. When an inducible promoter is included in the construct encoding an dsRNA, expression is assayed upon delivery to the subject of an appropriate dose of the substance used to induce expression.

Appropriate doses of a composition depend upon the potency of the molecule (the sequence encoding the dsRNA) with respect to the expression or activity to be modulated. One or more of these molecules can be administered to an animal (e.g., a human) to modulate expression or activity of one or more target polypeptides. A physician may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The efficacy of treatment can be monitored either by measuring the amount of the Bcl-2 target gene mRNA (e.g. using real time PCR) or the amount of polypeptide encoded by the target gene mRNA (Western blot analysis). In addition, the attending physician will monitor the symptoms associated with pancreatic cancer afflicting the patient and compare with those symptoms recorded prior to the initiation of dsRNA treatment.

We claim:

1. A method for inhibiting the expression of an anti-apoptotic gene in a cell, the method comprising: (a) introducing into the cell in vitro a double-stranded ribonucleic acid (dsRNA), wherein the dsRNA consists of less than 25 nucleotides in length and comprises a complementary RNA strand comprising a complementary nucleotide sequence which is complementary to at least a part of the Bcl-2 gene, and wherein the complementary nucleotide sequence consists of at least 24 nucleotides in length and comprises SEQ ID NO:2;

and (b) maintaining the cell produced in step (a) for a time sufficient to obtain degradation of the mRNA transcript of the anti-apoptotic gene, thereby inhibiting expression of the Bcl-2 gene in the cell.

2. A method for inhibiting the expression of an anti-apoptotic gene in a cell, the method comprising: (a) introducing into the cell in vitro a double-stranded ribonucleic acid (dsRNA), wherein the dsRNA consists of less than 25 nucleotides in length and comprises a complementary RNA strand comprising a complementary nucleotide sequence which is complementary to at least a part of the Bcl-2 gene, and wherein the complementary nucleotide sequence consists of at least 24 nucleotides in length and comprises SEQ ID NO:4; and (b) maintaining the cell produced in step (a) for a time sufficient to obtain degradation of the mRNA transcript of the anti-apoptotic gene, thereby inhibiting expression of the Bcl-2 gene in the cell.

3. The method of claim 1, wherein the dsRNA further comprises a sense RNA strand, and wherein at least one of the complementary RNA strand or sense RNA strand comprises a nucleotide overhang of 1 to 4 nucleotides in length, and wherein the sense RNA strand comprises the sequence of SEQ ID NO: 1.

4. The method of claim 2, wherein the dsRNA further comprises a sense RNA strand, and wherein at least one of the complementary RNA strand or sense RNA strand comprises a nucleotide overhang of 1 to 4 nucleotides in length, and wherein the sense RNA strand comprises the sequence of SEQ ID NO:3.

* * * * *

UNITED STATES PATENT AND TRADEMARK OFFICE
CERTIFICATE OF CORRECTION

| | | |
|---|---|---|
| PATENT NO. | : 7,473,525 B2 | Page 1 of 1 |
| APPLICATION NO. | : 10/384260 | |
| DATED | : January 6, 2009 | |
| INVENTOR(S) | : Kreutzer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1334 days.

Signed and Sealed this

Eighteenth Day of January, 2011

David J. Kappos
*Director of the United States Patent and Trademark Office*